US009271721B2

(12) United States Patent
Jimenez et al.

(10) Patent No.: US 9,271,721 B2
(45) Date of Patent: Mar. 1, 2016

(54) PORT CLOSURE DEVICE

(71) Applicant: Cook Medical Technologies LLC, Bloomington, IN (US)

(72) Inventors: Jorge Jimenez, Bloomington, IN (US); Jeffry T. Lasher, Bloomington, IN (US); Matthew J. Terwiske, Bloomington, IN (US); Lynne K. Nolte, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 19 days.

(21) Appl. No.: 14/107,675

(22) Filed: Dec. 16, 2013

(65) Prior Publication Data

US 2014/0171981 A1 Jun. 19, 2014

Related U.S. Application Data

(60) Provisional application No. 61/739,496, filed on Dec. 19, 2012.

(51) Int. Cl.
*A61B 17/04* (2006.01)
*A61B 17/00* (2006.01)
*A61B 17/062* (2006.01)
*A61B 17/06* (2006.01)
*A61B 19/00* (2006.01)

(52) U.S. Cl.
CPC ......... *A61B 17/0482* (2013.01); *A61B 17/0057* (2013.01); *A61B 17/0469* (2013.01); *A61B 2017/00637* (2013.01); *A61B 2017/00663* (2013.01); *A61B 2017/06042* (2013.01); *A61B 2019/5206* (2013.01)

(58) Field of Classification Search
CPC ........... A61B 17/0482; A61B 17/0483; A61B 17/06061; A61B 17/0485; A61B 17/0487; A61B 17/0281; A61B 17/04; A61B 17/062; A61B 2017/0409; A61B 2017/047; A61B 2017/00663; A61B 17/0057; A61B 17/0469; A61B 17/0491; A61B 17/3403; A61B 17/3423; A61B 17/3431; A61B 2017/00575; A61B 2017/00588; A61B 2017/00628; A61B 2017/00632; A61B 2017/0472; A61B 2017/0474; A61B 2017/00673; A61B 2017/3405; A61B 2017/3433; A61B 2017/3435; A61B 2017/3445; A61B 2017/3447; A61B 2017/3449
USPC ................. 606/148, 144, 150, 139, 213, 232, 606/153–155, 108; 600/184, 200, 417, 429
See application file for complete search history.

(56) References Cited

U.S. PATENT DOCUMENTS 5,368,601 A 11/1994 Sauer et al.
5,476,470 A 12/1995 Fitzgibbons, Jr.
(Continued)

FOREIGN PATENT DOCUMENTS

WO WO 2010081096 A2 * 7/2010

*Primary Examiner* — Katrina Stransky
*Assistant Examiner* — Katherine Schwiker
(74) *Attorney, Agent, or Firm* — Brinks Gilson & Lione

(57) ABSTRACT

The present invention provides devices for safely closing an opening in tissue using suture. In one embodiment, the device includes an elongated main body constructed to permit visualization longitudinally through the main body from the proximal end to the distal end, the distal end defining a support surface to support the suture and protect distal body structures. A flange is connect to the main body adjacent the proximal end and projects laterally therefrom in first and second lateral directions. First and second guide holes extend longitudinally through the flange, and are structured to direct a suturing instrument longitudinally towards the support surface for passing the suture.

21 Claims, 8 Drawing Sheets

(56) References Cited

U.S. PATENT DOCUMENTS

| | | |
|---|---|---|
| 5,836,955 A | 11/1998 | Buelna et al. |
| 2006/0030868 A1* | 2/2006 | Bennett .................. 606/148 |
| 2008/0097485 A1* | 4/2008 | Shpaichler et al. ......... 606/148 |
| 2011/0112557 A1* | 5/2011 | Beeley .................. 606/148 |
| 2011/0270282 A1* | 11/2011 | Lemke .................. 606/148 |
| 2012/0035623 A1* | 2/2012 | Bagaoisan et al. ......... 606/144 |
| 2012/0265223 A1* | 10/2012 | Shpaichler et al. ......... 606/148 |
| 2013/0253543 A1* | 9/2013 | Heneveld .................. 606/148 |

* cited by examiner

PORT CLOSURE DEVICE

CROSS-REFERENCE TO RELATED APPLICATIONS

This application claims the benefit of U.S. Provisional Application Ser. No. 61/739,496 filed on Dec. 19, 2012, entitled "PORT CLOSURE DEVICE" the entire contents of which are incorporated herein by reference.

FIELD OF THE INVENTION

The present invention relates generally to suturing percutaneous openings, such as openings used to access an internal organ, body cavity or bodily lumen, such as in laparoscopy or gastropexy.

BACKGROUND OF THE INVENTION

Among the most significant advances in medical surgical techniques has been the adoption, and now-routine performance, of a variety of minimally invasive procedures. These minimally invasive procedures are distinguishable from conventional open surgical procedures in that access to a body cavity of a patient is achieved through a relatively small incision through the tissue, such as the skin and underlying fascia layers. A tubular medical device (or tubular portion of a device) may be inserted or introduced through the incision into the body cavity for carrying out a medical procedure. Laparoscopy is one such procedure and is commonly used to treat a variety of internal bodily structures. Many other types of external percutaneous connections also provide a patient or medical staff with access to an internal organ or bodily lumen. For example, semi-permanent connections are made through the skin for placement of IV lines, catheters, dialysis lines, colostomy bags in the like. Percutaneous endoscopic gastrostomy tubes, commonly known as PEG tubes, are used as a means of feeding when a person is unable to eat. Gastropexy is a procedure to suture the stomach to the skin around and access site, e.g. for longer term placement of such connection tubes.

The puncture at the access site is typically closed by suturing, or by manually providing pressure on the site until clotting and/or wound sealing occurs. Suturing is more often utilized for larger punctures, whereas manual pressure is more often utilized in connection with smaller punctures. The manual method, however, can take half an hour or more, and requires the patient to remain substantially immobilized for at least that period of time while pressure is applied by medical personnel to the access site. In addition, it may be necessary for the patient to remain in the hospital for a period of time thereafter for observation. Furthermore, there may be a possibility of clot formation at the puncture site.

Utilizing sutures to close the opening may have procedure variability, which may require additional time to close the vessel. When sutures are utilized to close a larger vascular access site, they typically are of the "purse-string" type. In this type of suture, a single thread is stitched to surround the access site, and then pulled tight (like a purse-string) to close the access site. Performing this suture typically requires a good deal of skill and practice on the part of the physician. It also may be difficult to perform this type of suturing in a key-hole type procedure, or in other types of surgery where there is limited access to the wound site. Damage to the underlying body structures is also a concern when suturing such openings, as is the proper suturing of the fascia layers beneath the skin.

BRIEF SUMMARY OF THE INVENTION

The present invention provides devices for safely closing an opening in tissue using sutures. In one embodiment, the device includes an elongated main body having a sidewall extending from a proximal end to a distal end and defining a longitudinal axis extending therebetween. The main body is constructed to permit visualization longitudinally through the main body from the proximal end to the distal end, the distal end defining a support surface. A flange is connect to the main body adjacent the proximal end and projects laterally therefrom in first and second lateral directions. A first wing of the flange projects in the first direction and has a first guide hole extending longitudinally therethrough, while a second wing of the flange projects in the second direction and has a second guide hole extending longitudinally therethrough. The first guide hole is structured to direct a suturing instrument longitudinally through the first guide hole towards the support surface, and the second guide hole is also structured to direct the suturing instrument longitudinally through the second guide hole towards the support surface.

According to further detailed aspects, the first and second guide holes are laterally spaced away from the longitudinal axis. The sidewall defines an access opening adjacent the distal end that is structured to provide access to the support surface from an exterior of the sidewall. The support surface is positioned along the longitudinal axis, and preferably includes a longitudinally facing surface. The support surface may further include a laterally facing surface connected to the longitudinally facing surface. Optionally, the support surface may define a catch structured to engage a suture.

According to still further detailed aspects, the sidewall of the main body is preferably a tubular member defining an interior space. The sidewall may include an access hole adjacent the proximal end to provide access to the interior space. The main body includes a proximal end wall closing off a proximal section of the main body, and includes a distal end wall closing off a distal section of the main body. The distal end wall is positioned proximal to the support surface.

In one construction, the first wing of the flange is longitudinally spaced away from the support surface a first height, and the first guide hole is laterally spaced away from the longitudinal axis a first width, and the guide hole extends longitudinally along a first guide axis that is angled relative to the longitudinal axis such that the first guide axis intersects the longitudinal axis adjacent the support surface. Likewise, the second wing of the flange may be longitudinally spaced away from the support surface a second height, while the second guide hole is laterally spaced away from the longitudinal axis a second width, and the guide hole extends longitudinally along a second guide axis that is angled relative to the longitudinal axis such that the second guide axis intersects the longitudinal axis adjacent the support surface. In another construction, the first wing of the flange is longitudinally spaced away from the support surface a first height, and the first guide hole is laterally spaced away from the longitudinal axis a first width, wherein the first guide axis is generally parallel to the longitudinal axis to accommodate a curved suturing instrument.

In another embodiment, a medical system is provided for closing an opening in tissue. The medical system includes a first elongate suturing instrument having a first operative end and a suture releasably connected thereto. An elongated main body has a sidewall extending from a proximal end to a distal end and defines a longitudinal axis extending therebetween. The main body is constructed to permit visualization longitudinally through the main body from the proximal end to the distal end, where the distal end defines a support surface. A flange is connect to the main body adjacent the proximal end and projects laterally therefrom in first and second lateral directions. A first wing of the flange projects in the first direction and has a first guide hole extending longitudinally therethrough. A second wing of the flange projects in the second direction and has a second guide hole extending longitudinally therethrough. The medical system has a first deployed configuration wherein the first suturing instrument passes longitudinally through the first guide hole and tissue such that its first operative end is located adjacent the support structure to leave the suture of a distal side of the tissue. The medical system has a second deployed configuration wherein one of the first suturing instrument and a second elongate suturing instrument having a second operative end passes longitudinally through the second guide hole and its operative end is located adjacent the support structure.

In one construction, the first suturing instrument extends in a straight line, and the first guide hole extends longitudinally along a first guide axis that is angled relative to the longitudinal axis such that the first guide axis intersects the longitudinal axis adjacent the support surface. In another construction, the first guide hole is laterally spaced away from the longitudinal axis, and the first suturing instrument is curved. Here, the first guide hole extends longitudinally along a first guide axis that is generally parallel to the longitudinal axis. The guide hole may be elongated in the lateral direction, while tapering inwardly in a distal longitudinal direction.

DETAILED DESCRIPTION OF THE INVENTION

The terms "proximal" and "distal" as used herein are intended to have a reference point relative to the user. Specifically, throughout the specification, the terms "distal" and "distally" shall denote a position, direction, or orientation that is generally away from the user and towards a target site, and the terms "proximal" and "proximally" shall denote a position, direction, or orientation that is generally towards the user and away from a target site. Thus, "proximal" and "distal" directions, portions of a device, or bodily regions, may depend on the point of entry for the procedure (e.g., percutaneously or laparoscopically or endoscopically).

Figure 1:
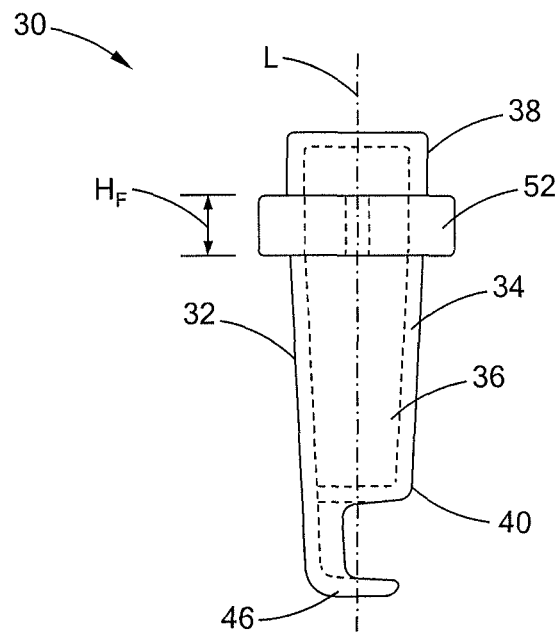
FIG. 1 is a side view of a medical device for closing and opening in tissue.
Figure 2:
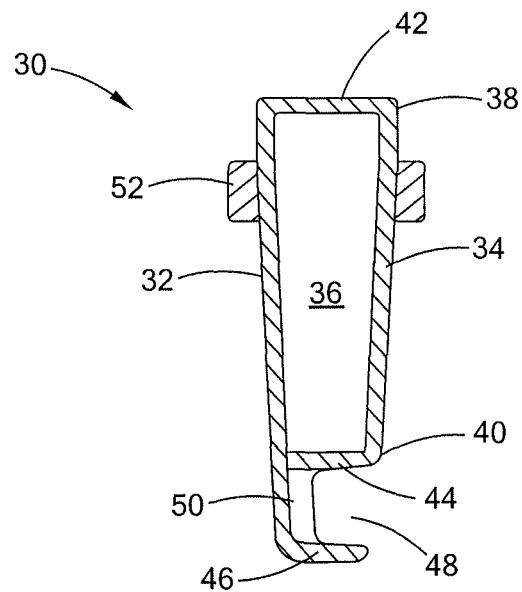
FIG. 2 is a cross-sectional view of the device shown in FIG. 1, taken from the side.
Figure 3:
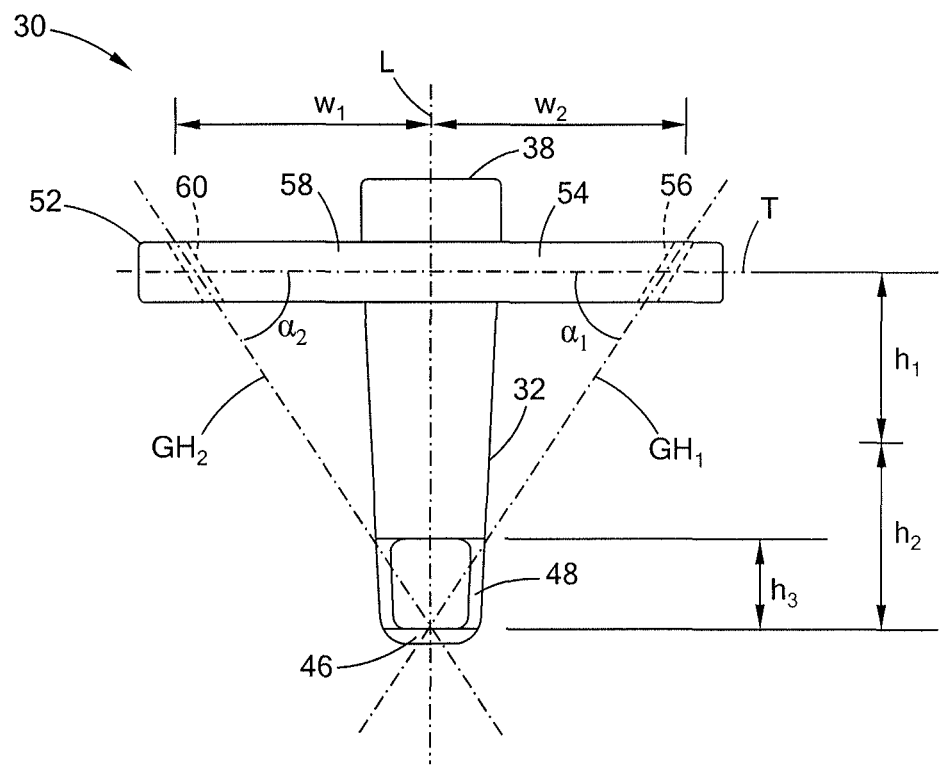
FIG. 3 is front view of the device of FIG. 1.
Figure 5:
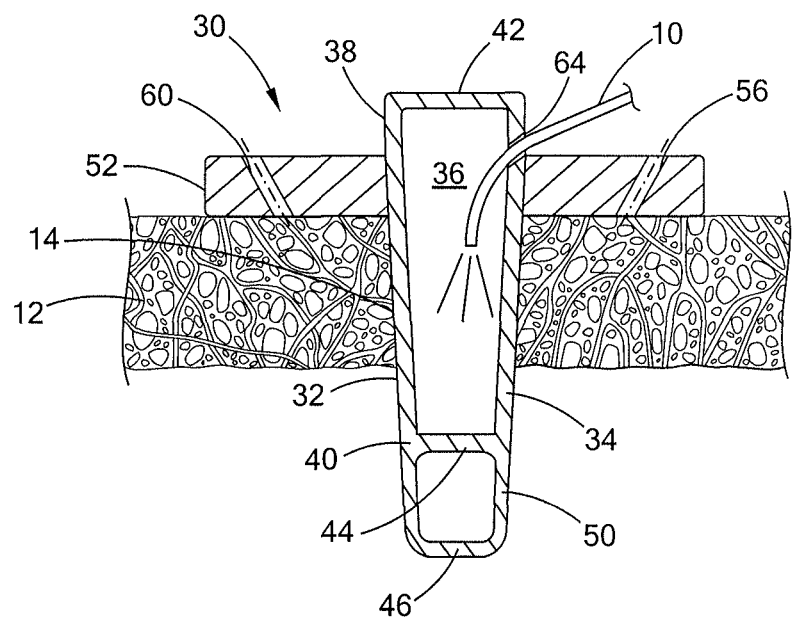
FIG. 5 is a cross-sectional view of the device of FIG. 1, taken from the front and showing the device applied to the opening in the tissue.

Turning now to the figures, FIGS. 1-3 depict a medical device 30 for closing an opening in tissue 12 (FIG. 5). The medical device 30 generally includes an elongated main body 32 defined by a side wall 34, which in the depicted embodiment is tubular and defines an interior space 36. The main body 32 and side wall 34 extend from a proximal end 38 to a distal end 40 and define a longitudinal axis L extending therebetween. As best seen in FIG. 2, the main body 32 further includes a proximal end wall 42 and a distal end wall 44 to enclose the interior space 36.

Preferably the medical device 30 is manufactured using injection molding and high density polyethylene or other hard plastic. In particular, the material is preferably a clear plastic to permit visualization longitudinally through the main body 32 from the proximal end 38 to the distal end 40. However, it will also be recognized that only the proximal end wall 42 and distal end wall 44 may be formed of a clear material, such as another clear plastic or optical glass (which can be magnifying) to enclose the interior space 36 while permitting visualization therethrough. The side wall 34 preferably has a circular cross-section that slightly narrows as it extends distally, and preferably has an average outer diameter of about 2 cm. The flange preferably has a longitudinal thickness of about 5 mm. The proximal end wall 42 preferably has a diameter of about 1.5 cm. The side wall 34 preferably has a thickness of about 0.25 cm.

The main body 32 also defines a support surface 46 at a location distally beyond the distal end wall 44. Generally, the support surface faces longitudinally and is used to support suturing while protecting body structures located distal to the medical device 30. The side wall 34 extends distally beyond the distal end wall 44 and is connected to the support surface 46. In particular, the side wall 34 includes an access opening 48 distal to the distal end wall 44 which provides access to the support surface 46 from the exterior of the device 30. In particular, the access opening 48 extends from a front of the device 30 around to opposing lateral sides such that the support surface 46 may be accessed from two opposing lateral sides of the device 30. The remaining portion 50 of the side wall 34 generally forms an L-shape with the support surface 46 as best seen in FIGS. 1 and 2. A portion of the lateral sides may also remain as shown in the figures (e.g. about 180 to 250 degrees of the side wall 34 may be removed to form the opening 48).

The medical device 30 also includes a flange 52 which extends in laterally opposite directions away from the longitudinal axis L and away from the main body 32, and defines a transverse axis T. The lateral length of the flange 52 is preferably about 1 cm to 10 cm. A first wing 54 of the flange 52 defines a first guide hole 56 that extends longitudinally therethrough, and similarly a second wing 58 of the flange (projecting in a laterally opposite direction from the first wing 54) defines a second guide hole 60 extending longitudinally therethrough. The first guide hole 56 is spaced a first width $w_1$ away from the longitudinal axis L and is angled relative to the longitudinal axis L. As shown in FIG. 3, the first guide hole 56 extends along a guide hole axis $GH_1$ that is angled relative to the transverse axis T by an angle $\alpha_1$. Likewise, the second guide hole 60 extends along a guide hole axis $GH_2$ that is angled relative to the transverse axis T by an angle $\alpha_2$. The dimensions of $w_1$, $w_2$, $\alpha_1$, $\alpha_2$ are selected such that the guide hole axis $GH_1$ and $GH_2$ intersect the longitudinal axis L at a point near the support surface 46. As will be described further hereinbelow, this structure allows suturing needles or other suturing instruments to be placed through the guide holes 56, 60 and guided to the support surface 46 where the suture can be exchanged while the underlying body structures are protected.

As also seen in FIG. 3, a first height $h_1$ depicts a typical height (also referred to as depth) of the skin and tissue being sutured (see, e.g., tissue 12 in FIG. 5). This height has been shown to the transverse axis T, although the tissue will generally contact the distal surface of the flange 52 and thus $h_1$ can also refer to this distance. At the same time, the tissue may become slightly compressed when employing the device 30 and thus $h_1$ may be selected according to a known range of variation. A second height $h_2$ refers to the remaining length of the medical device 30, and is generally the distance between the support surface 46 and the distal side (or interior side) of the tissue. A height $h_3$ refers to the longitudinal height of the openings 48 formed in the side wall 34 of the main body 32 which provides access to the support surface 46 from the lateral sides of the main body 32.

The lateral location of the first and second guide holes 56, 60 ($w_1$, $w_2$) and the height of the access opening 48 ($h_3$) are selected such that the guide hole axes ($GH_1$ and $GH_2$) define a clear path to the support surface 46. The free depth ($h_2$) of the main body 32 (i.e. the depth below the tissue) is selected to be sufficiently long so that the path the needle makes through the tissue (generally defined here as $GH_1$ and $GH_2$) extends entirely through the tissue and does not pass radially through the already formed opening 14 in the tissue 12 (see FIG. 4). Preferably, the height $h_2$ is selected to be about equal to (i.e. within 15%) the height $h_1$ to achieve the foregoing. Preferably, the combined height $h_1+h_2$ is in the range of about 10 to 30 cm. That is, the medical device 30 may come in various sized for different types (thicknesses) of tissue, for example 10 cm, 15 cm, 20 cm, 25 cm in total height. As such, the lateral spacing ($w_1$, $w_2$) of the first and second guide holes 56, 60 is accordingly adjusted. The angles $\alpha_1$, $\alpha_2$ may likewise be adjusted for each size device but preferably remains in a range of about 15 to 45 degrees.

Figure 4:
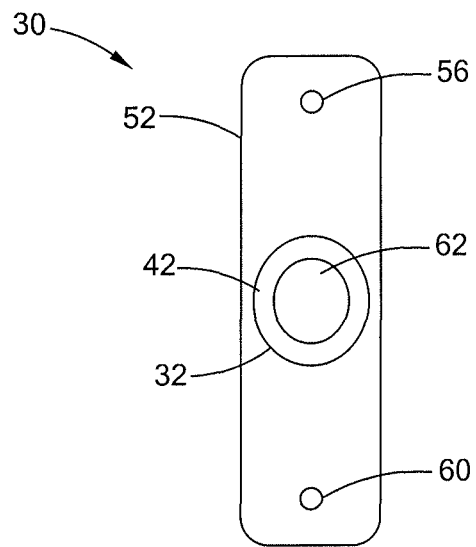
FIG. 4 is a top view of the device of FIG. 1.

As shown in the top view of FIG. 4, the flange 52 generally defines first and second guide holes 56, 60 spaced laterally away from the main body 32. The proximal end wall 42 provides visualization straight through the device 30, and in particular down to the support surface 46 where the guide axes $GH_1$ and $GH_2$ intersect each other and the longitudinal axis L. The proximal end wall 42 may further include a magnifying element 62 which provides enhanced viewing of the suture passing that will be taking place at the support surface 46. Similarly, as shown in FIG. 5, the main body 30 and its side wall 32 may further define a visualization port 64 at or proximal to the flange 52 which provides access to the interior space 36. In particular, a visualization element 10 (such as a small scope or fiber-optic visualization device) may be inserted through the hole 64 to get closer to and more clearly visualize the distal end 44 of the medical device 30. As can also be seen in FIG. 5, the side wall 34, proximal end wall 42 and distal end wall 44 generally create a seal with the tissue 12 in its opening 14 such that fluids or gases cannot pass through the opening 14. At the same time, the flange 52 controls the medical device 30 relative to the tissue 12, and its guide holes 56, 60 can guide a suturing instrument through the tissue 12 and distally to the support surface 46 located below the tissue 12 for exchange of sutures, anchors or other tissue closing devices.

Figure 6:
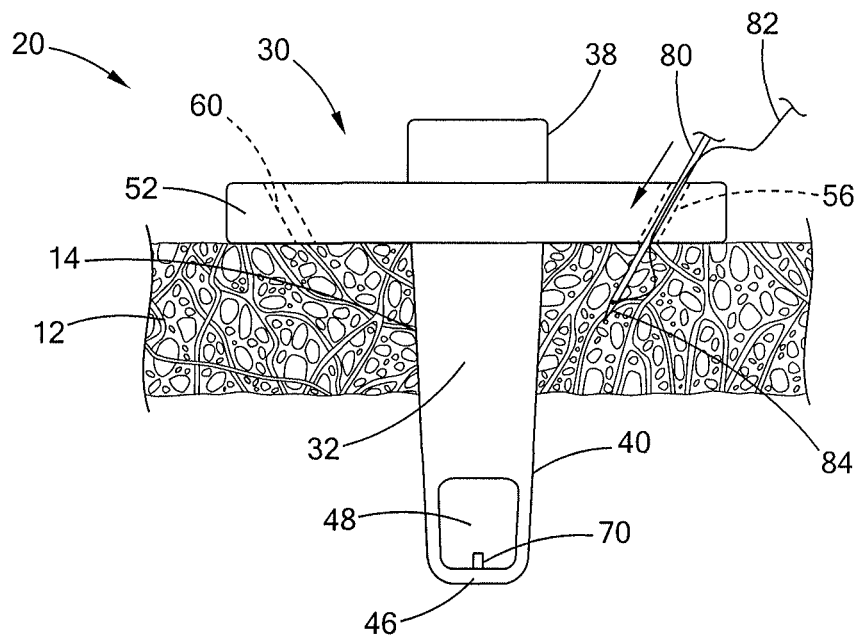
FIG. 6 is a front view of a medical system employing the medical device of FIG. 1, and depicting operation thereof.

Operation of the medical system 20 and the medical device 30 will now be described with reference to FIGS. 6-14. As shown in FIG. 6, the medical device 30 is placed within the opening 14 in the tissue 12 such that the flange 52 abuts a proximal surface of the tissue 12 and the main body 32 extends through the opening 14 such that its distal end 40 is positioned distally beyond the tissue 12. In addition to the medical device 30, the medical system 20 includes a suturing element which has been depicted in the figures as a suturing needle 80. The needle 80 carries a suture 82 at its distal (operative) end 84, e.g. using a slot, hole or simply having the suture 82 running though the needle 80. The needle 80 is passed distally through the first guide hole 56 such that it pierces the tissue 12 as shown in FIG. 6.

Figure 7:
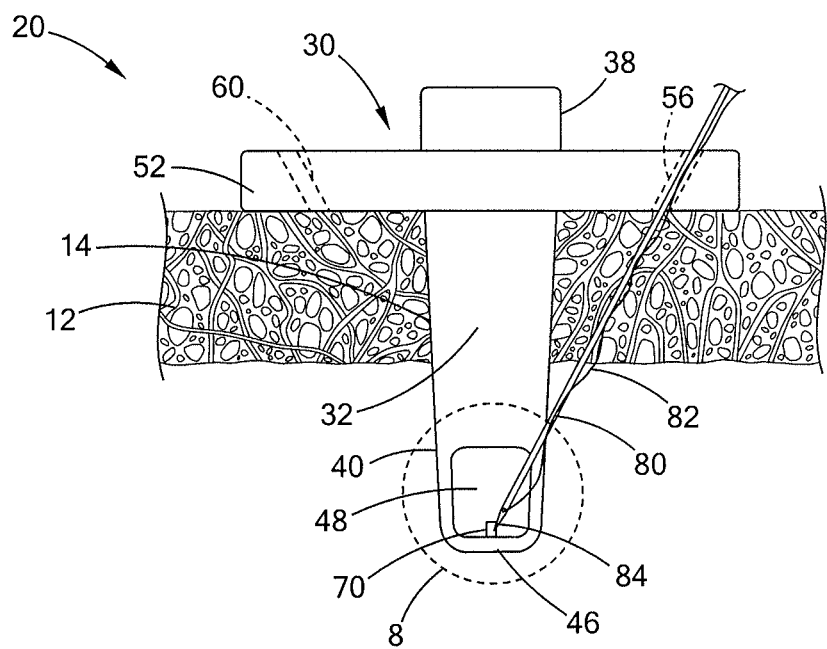
FIG. 7 is a front view of a medical system depicted in FIG. 6, showing further operation thereof.
Figure 8:
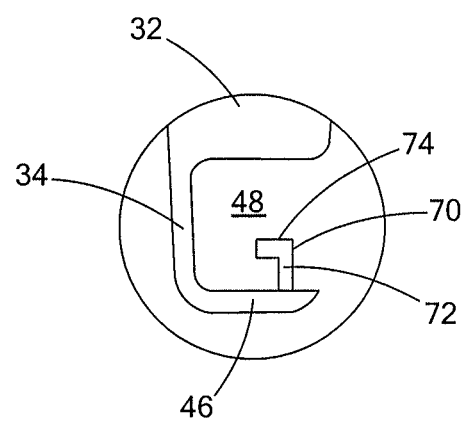
FIG. 8 is an enlarged side view of the area denoted by the circle 8 in FIG. 7.

As shown in FIG. 7, the needle 80 continues to move distally through the tissue 12 and along the exterior of the main body 32 of the medical device 30. The needle 80 continues to be moved until it passes through the access opening 48 in the side wall 34, and preferably until it reaches the support surface 46. At this point, the suture 82 may be held in place while the needle 80 is moved proximally to leave the suture 82 at the distal end 40 of the medical device 30, e.g. laying on the support surface 46.

Preferably, the medical device 30 and its support surface 46 may further include a suture catch 70 designed to facilitate engagement of the suture 82 with the support surface 46. As best seen in the enlarged view of FIG. 8, the suture catch 70 may simply include an L-shaped tab comprising a longitudinal leg 72 and a lateral leg 74. Many variations of the catch 70 will be readily apparent to the skilled artisan. For example, the catch 70 may simply include the longitudinal leg 72 with an optional slot or slit formed therein. Likewise magnetic elements may be utilized in conjunction with a magnetic element on the distal end of the suture 82.

Figure 9:
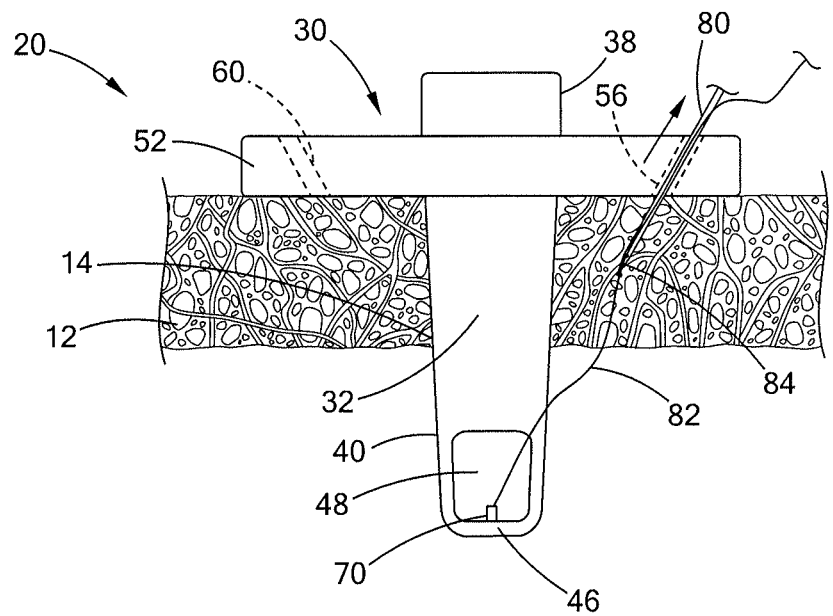
FIGS. 9-12 are front views of the medical system of FIG. 6 showing further operation thereof.
Figure 10:
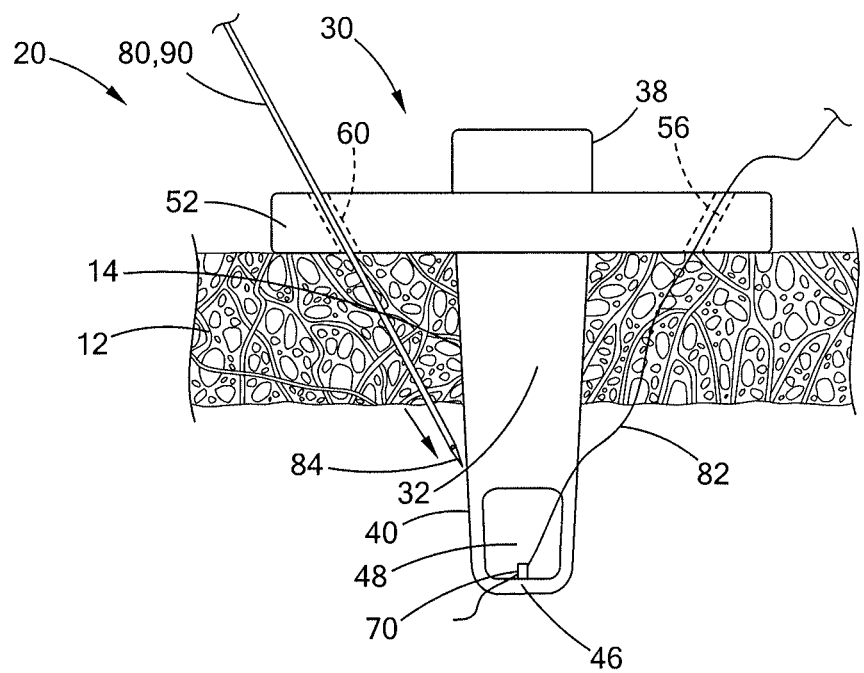

Turning now to FIG. 9, the needle 80 is moved proximally such that it passes again back through the tissue 12 and first guide hole 56 while the suture 82 remains at the distal end 40 of the medical device, preferably engaged with the support surface 46 and/or its catch 70. As shown in FIG. 10, the needle 80, or a second suturing instrument (such as a second needle 90) is passed through the second guide hole 60 in the flange 52 of the medical device 30. The second guide hole 60 directs the needle 80, 90 through the tissue 12 and along the exterior of the main body 32 until it reaches the access opening 48 at the distal end 40 of the medical device 30. While FIGS. 9 and 10 depict the first needle 80 being withdrawn proximally, it will be recognized that the first needle 80 could be left in the position shown in FIG. 7 while the second needle 90 is passed through the second guide hole 60. In such a case, the suture 82 may be passed directly from the first needle 80 to the second needle 90.

Figure 11:
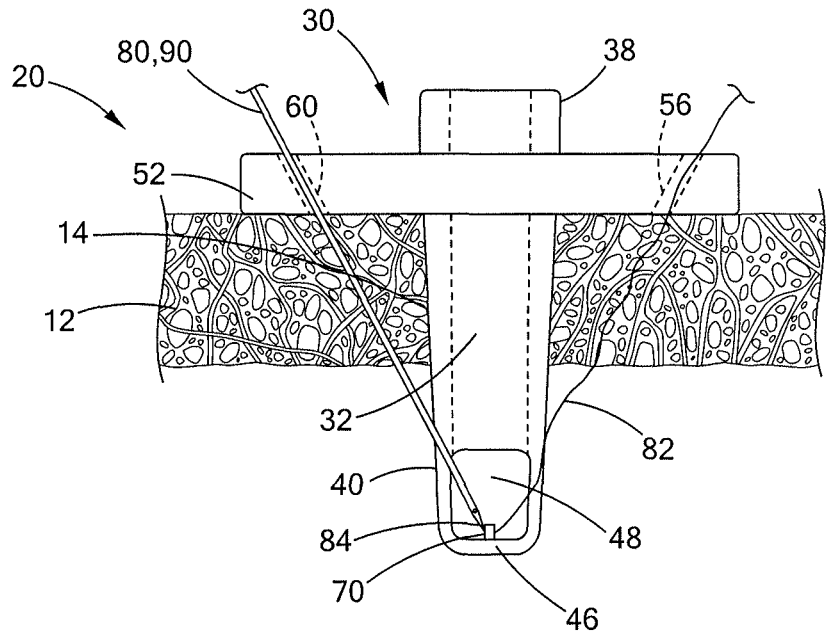
Figure 12:
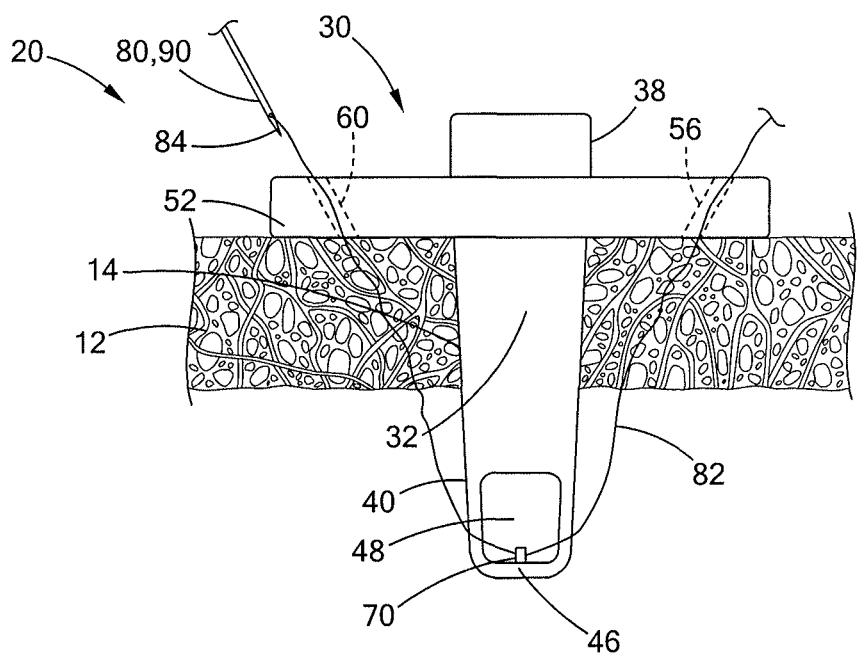

As shown in FIG. 11, the first and second needle 80, 90 is moved distally until it reaches the support surface 46 (and/or catch 70 if present) and is used to engage the suture 82. Again, the distal end of the needle 80, 90 preferably has structure for engaging the suture 82, although a snare or other grasping device may be used in conjunction with the needle 80, 90 and used to grasp the suture 82. As shown in FIG. 12, the needle 80, 90 is used to engage the suture 82 and pull it proximally back through the tissue 12 and second guide hole 60 until it is located proximal to the flange 52 for manipulation by the medical professional.

Figure 13:
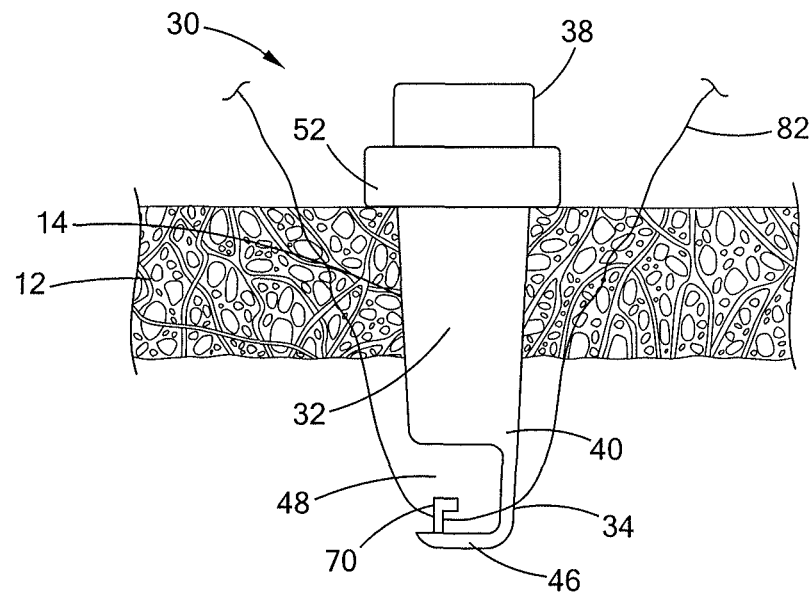
FIGS. 13 and 14 are side views of the medical system depicted in FIG. 6, showing further operation thereof.
Figure 14:
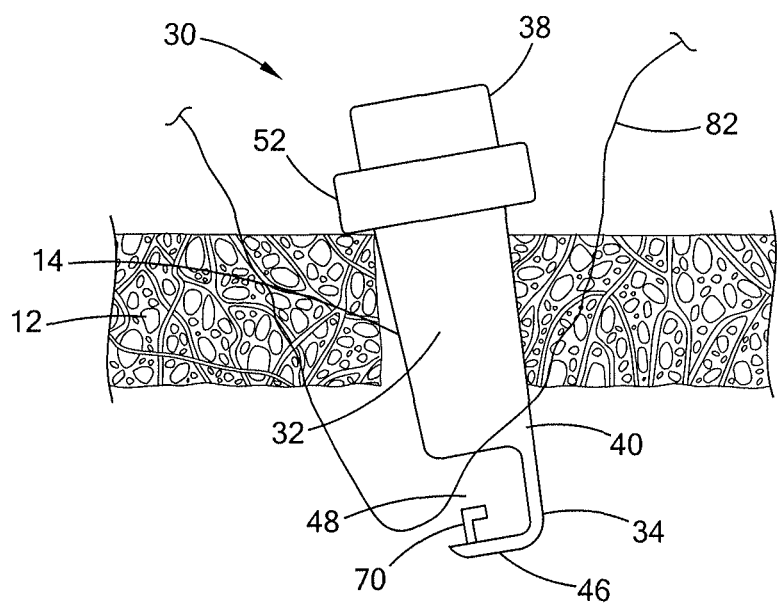

Turning now to FIGS. 13 and 14, the medical device 30 has been shown from the side, and still placed within the opening 14 and the tissue 12, and with the suture 82 extending distally through the tissue and looping back proximally again to the tissue at a second location opposite the opening 14 in the tissue 12. The medical device 30 may then be manipulated, such as by grasping the proximal end 38 and rotating it such that the suture 82 is released from the catch 70 or is otherwise moved through the access opening 48 in the main body 32. Typically this rotation will be about a transvers axis such the axis T shown, although it may also include rotation about the longitudinal axis L and/or twisting and rocking. The medical device 30 may then be moved proximally back through the opening 14 and the suture 82 to be manipulated to close the opening 14 in the tissue 12.

Figure 15:
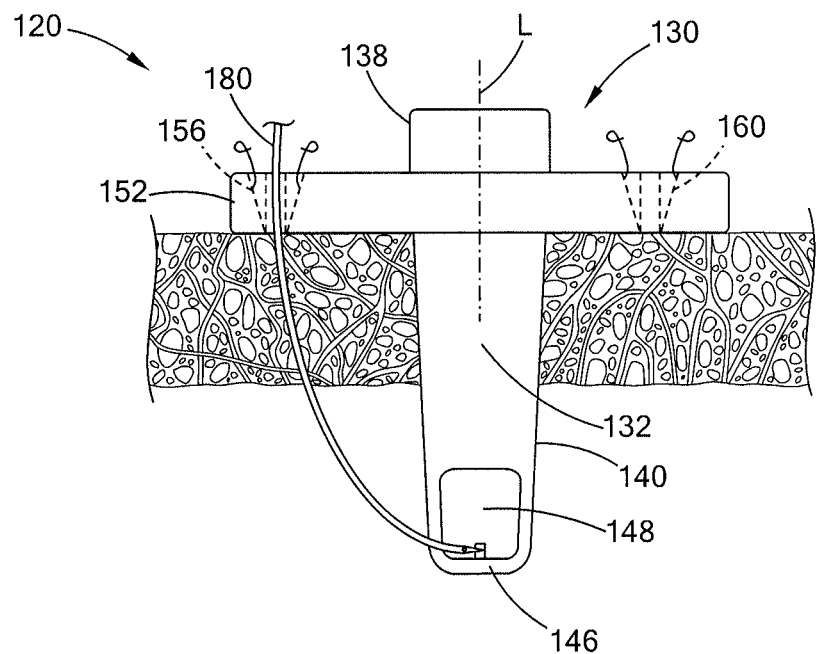
FIG. 15 is a front view of an alternate embodiment of the medical system of FIG. 6.
Figure 16:
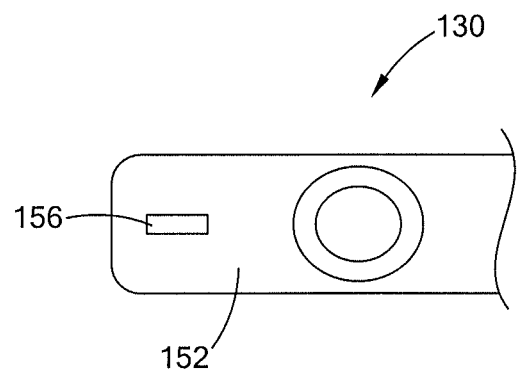
FIG. 16 is a top view, partially cut-away, of the medical device forming a portion of the medical system of FIG. 15.

FIGS. 15 and 16 show an alternate embodiment of the medical system 120 and medical device 130. The medical system 120 and device 130 are substantially similar to the previous embodiment, and similar reference numerals (but in the hundreds) have been used, and only the notable differences will be discussed herein. In this embodiment, the suturing instrument 180 (or instruments) are curved, such as a curved needle. Other suturing instruments that are capable of bending, such as a bendable trocar or piercing catheter, may likewise be used. The first and second guide holes 156, 160 are similarly adapted for use with a curved suturing instrument 180. In particular, the first and second guide holes 156, 160 are preferably aligned to extend longitudinally parallel to the longitudinal axis L. Further, the guide holes preferably narrow or taper in the distal direction. As best seen in the top view of FIG. 16, (only the first guide hole 156 being shown) the guide holes 156, 160 are preferably elongated in a lateral direction. Stated another way, the guide holes 156, 160 have a larger lateral width at their proximal end which reduces in size as the holes move distally through the flange 152. This structure promotes placement of the curved needle 180 through the guide holes 156, 160 in a manner such that the curvature is concavely facing the main body 132, which assists the user in placing the needle 180 through the guide holes 156, 160 such that the needle extends distally through the tissue 12 and curves laterally inwardly towards the longitudinal axis L. That is, such that the curved needle 180 passes through access opening 148 and crosses the longitudinal axis L at or near the support surface 146. It will also be recognized that in this embodiment the first and second guide holes 156, 160 may be placed laterally closer to the main body 132 while still insuring that the needle 180 passes fully through the tissue 12 without passing through a lateral surface of the opening 14 formed in the tissue 12.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for closing an opening in tissue using a suturing instrument having a suture, the medical device comprising:
    an elongated main body having a sidewall extending from a proximal end to a distal end and defining a longitudinal axis extending therebetween, the distal end defining a support surface for the suturing instrument, the support surface having an exposed longitudinally facing surface, the main body constructed to permit visualization longitudinally through the main body from the proximal end to the distal end and the support the surface;
    a flange connected to the main body adjacent the proximal end and projecting laterally therefrom in first and second lateral directions, a first wing of the flange projecting in the first direction and having a first guide hole extending longitudinally through the first wing, a second wing of the flange projecting in the second direction and having a second guide hole extending longitudinally through the second wing; and
    the first guide hole structured to direct the suturing instrument longitudinally through the first guide hole along a first guide path towards the longitudinally facing surface of the support surface, the second guide hole structured to direct the suturing instrument longitudinally through the second guide hole along a second guide path towards the longitudinally facing surface of the support surface, the first and second guide paths intersecting directly adjacent the support surface distal to the tissue.

2. The medical device of claim 1, wherein the first and second guide holes are laterally spaced away from the longitudinal axis.

3. The medical device of claim 1, wherein the sidewall defines an access opening at the distal end, the access opening structured to provide access to the support surface from an exterior of the sidewall.

4. The medical device of claim 1, wherein the support surface further includes a laterally facing surface connected to the longitudinally facing surface.

5. The medical device of claim 1, wherein the support surface defines a raised catch structured to engage a suture.

6. The medical device of claim 1, wherein the sidewall of the main body is a tubular member defining an interior space.

7. The medical device of claim 6, wherein the sidewall includes an access hole at the proximal end to provide access to the interior space and the longitudinally facing surface.

8. The medical device of claim 6, wherein the main body includes a proximal end wall closing off the interior space at a proximal section of the main body.

9. The medical device of claim 1, wherein the main body includes a distal end wall closing off a distal section of the main body.

10. The medical device of claim 9, wherein the distal end wall is positioned proximal to the support surface.

11. The medical device of claim 1, wherein the first wing of the flange is longitudinally spaced away from the support surface by a first height, and the first guide hole is laterally spaced away from the longitudinal axis by a first width, and wherein the first guide hole extends longitudinally along a first guide axis that is angled relative to the longitudinal axis such that the first guide axis intersects the longitudinal axis immediately adjacent the support surface.

12. The medical device of claim 11, wherein the second wing of the flange is longitudinally spaced away from the support surface by a second height, and the second guide hole is laterally spaced away from the longitudinal axis by a second width, and wherein the second guide hole extends longitudinally along a second guide axis that is angled relative to the longitudinal axis such that the second guide axis intersects the longitudinal axis adjacent the support surface.

13. The medical device of claim 1, wherein the first wing of the flange is longitudinally spaced away from the support surface a first height, and the first guide hole is laterally spaced away from the longitudinal axis a first width, and wherein the first guide axis is generally parallel to the longitudinal axis to accommodate a curved suturing instrument.

14. The medical device of claim 1, wherein the first guide hole is laterally spaced away from the longitudinal axis, and wherein the first suturing instrument is curved.

15. The medical device of claim 14, wherein the first guide hole extends longitudinally along a first guide axis that is generally parallel to the longitudinal axis.

16. The medical device of claim 14, wherein the first guide hole is elongated in the lateral direction, and tapers inwardly in a distal direction.

17. The medical device of claim 1, wherein the support surface is positioned to abut and stop distal movement of the suturing instrument passing through either of the first and second guide holes.

18. A medical system for closing an opening in tissue comprising:
 a first elongate suturing instrument having a first operative end and a suture releasably connected thereto;
 an elongated main body having a sidewall extending from a proximal end to a distal end and defining a longitudinal axis extending therebetween, the main body constructed to permit visualization longitudinally through the main body from the proximal end to the distal end, the distal end defining a support surface;
 a flange connect to the main body adjacent the proximal end and projecting laterally therefrom in first and second lateral directions, a first wing of the flange projecting in the first direction and having a first guide hole extending longitudinally through the first wing, a second wing of the flange projecting in the second direction and having a second guide hole extending longitudinally through the second wing; and
 the medical system having a first deployed configuration wherein the first suturing instrument passes longitudinally through the first guide hole and tissue and the first operative end is located at a first position adjacent the support surface to leave the suture on a distal side of the tissue, the medical system having a second deployed configuration wherein one of the first suturing instrument and a second elongate suturing instrument having a second operative end passes longitudinally through the second guide hole and its operative end is located at the first position adjacent the support surface such that the second operative end is positioned to engage the suture on the distal side of the tissue; wherein the first guide hole is structured to direct the suturing instrument longitudinally along a first guide path, and the second guide hole is structured to direct the suturing instrument longitudinally along a second guide path, and wherein the first guide path and the second guide path intersect at an intersection point directly adjacent the support surface and distal to the tissue.

19. The medical system of claim 18, wherein the first suturing instrument extends in a straight line, and wherein the first guide hole extends longitudinally along a first guide axis that is angled relative to the longitudinal axis such that the first guide axis intersects the longitudinal axis immediately adjacent the support surface.

20. The medical device of claim 18, wherein the intersection point is located where the longitudinal axis meets the support surface.

21. The medical system of claim 18, wherein the first position is a point in space.

* * * * *